United States Patent
Beebe et al.

(10) Patent No.: US 7,189,581 B2
(45) Date of Patent: Mar. 13, 2007

(54) METHOD OF OBTAINING A SAMPLE CONCENTRATION OF A SOLUTION IN A MICROFLUIDIC DEVICE

(75) Inventors: David J. Beebe, Madison, WI (US); Glenn M. Walker, Brentwood, TN (US)

(73) Assignee: Wisconsin Alumni Research Foundation, Madison, WI (US)

(*) Notice: Subject to any disclaimer, the term of this patent is extended or adjusted under 35 U.S.C. 154(b) by 638 days.

(21) Appl. No.: 10/425,219

(22) Filed: Apr. 29, 2003

(65) Prior Publication Data

US 2003/0203506 A1 Oct. 30, 2003

Related U.S. Application Data

(60) Provisional application No. 60/376,609, filed on Apr. 30, 2002.

(51) Int. Cl.
*G01N 1/10* (2006.01)
*G01N 1/00* (2006.01)
*B01L 3/02* (2006.01)
*B32B 5/02* (2006.01)
*B32B 27/04* (2006.01)

(52) U.S. Cl. .................. 436/180; 422/50; 422/68.1; 422/100; 422/103; 436/43; 436/52; 436/53; 137/8; 137/9; 137/12; 137/14

(58) Field of Classification Search ............... 422/50, 422/100, 68.1, 101, 102, 103; 436/43, 52, 436/53, 180; 137/8, 9, 12, 14; 417/48
See application file for complete search history.

(56) References Cited

U.S. PATENT DOCUMENTS

| 6,174,675 B1* | 1/2001 | Chow et al. ................... 435/6 |
| 6,210,128 B1* | 4/2001 | Rife et al. .................. 417/322 |
| 6,224,728 B1* | 5/2001 | Oborny et al. .............. 204/450 |
| 6,739,576 B2* | 5/2004 | O'Connor et al. ..... 251/129.14 |
| 6,767,706 B2* | 7/2004 | Quake et al. .................. 435/6 |

* cited by examiner

*Primary Examiner*—Brian Sines
(74) *Attorney, Agent, or Firm*—Boyle Fredrickson Newholm Stein & Gratz S.C.

(57) ABSTRACT

A method is provided of obtaining a sample concentration of a solution in a microfluidic device. The microfluidic device includes a channel having a reservoir and a collection port. The channel is filled with a solution having particles therein. A reservoir drop is deposited over the reservoir of the channel such that the solution of the channel flows towards the collection port in response to evaporation of the solution at the collection port. The particles at the collection port are collected to obtain the sample concentration.

22 Claims, 1 Drawing Sheet

METHOD OF OBTAINING A SAMPLE CONCENTRATION OF A SOLUTION IN A MICROFLUIDIC DEVICE

CROSS-REFERENCE TO RELATED APPLICATIONS

This application claims the benefit of U.S. Provisional Application Ser. No. 60/376,609, filed Apr. 30, 2002.

REFERENCE TO GOVERNMENT GRANT

This invention was made with United States government support awarded by the following agencies: DOD ARPA F30602-00-2-0570.

FIELD OF THE INVENTION

This invention relates generally to microfluidic devices, and in particular, to a method of obtaining a sample concentration of particles from a solution in a microfluidic device.

BACKGROUND AND SUMMARY OF THE INVENTION

As is known, microfluidic devices are being used in an increasing number of applications including various traditional laboratory tasks. These tasks are implemented at the microscale level in order to realize the potential of comprehensive lab-on-a-chip (LOC) components such as pumps, filters, and mixers. These LOC components may be coupled together in various ways to accomplish tasks such as aliquoting specific volumes of liquid into a microchannel or mixing together reagents and observing the result in a detection microchannel. A task that has received only limited attention thus far is sample concentration.

The ability of microfluidic systems to manipulate small volumes of fluid is one of the strengths of such systems. However, since only small volumes of fluid are manipulated, the concentrations of molecules in the fluid are difficult to detect. It can be appreciated that obtaining a sample concentration of molecules in fluid flowing through the microfluidic system is a necessary task in almost any LOC system. Hence, it is highly desirable to provide a method of obtaining a sample concentration that is simple to incorporate into any microfluidic device design regardless of the method implemented for pumping fluid through a channel of a microfluidic device, the material from which the microfluidic device is constructed, or the nature of the sample (i.e., organic or inorganic) to be concentrated.

By way of example, the most common application wherein a sample concentration must be obtained is capillary electrophoresis (CE). The three most popular methods for obtaining the sample concentration in CE are: field-amplified sample stacking; isotachophoresis; and solid-phase extraction. Field-amplified sample stacking is performed by electrokinetically pulling a sample of fluid from a region of low buffer concentration into a region of high buffer concentration. The difference in buffer concentration affects the sample velocity by slowing or "stacking," the sample within the high concentration buffer adjacent the interface. Isotachophoresis involves the use of electrolytes of different mobility. The sample of fluid is positioned between so-called leading and trailing electrolytes. The sample separates into zones of different mobility wherein each zone has a concentration proportional to the leading electrolyte concentration. Solid-phase extraction involves the treatment of a surface or the packing of the microchannels of the microfluidic device with treated solids in order to attract the molecule of interest. A solution containing the molecules to be concentrated is flowed over the treated surface such that the molecules concentrate at the treated surface.

It can be understood that these prior methods require that the sample of fluid have an appropriate charge or that the molecules of the sampled fluid have the ability to be bound to a specific molecule. An alternate technique that is free from the constraints of prior methods is ultrasonic acoustic particle trapping. However, ultrasonic acoustic particle trapping requires complex microfabrication processing and can be difficult to integrate into microfluidic device designs. It can be appreciated that the ideal method of obtaining a sample concentration should incorporate all the benefits of the previous methods, heretofore described, without the drawbacks.

Therefore, it is a primary object and feature of the present invention to provide a method of obtaining a sample concentration of particles from a solution in a microfluidic device that is simple and inexpensive to implement.

It is a further object and feature of the present invention to provide a method of obtaining a sample concentration of particles from a solution in a microfluidic device that may be utilized with microfluidic devices of any design regardless of the method implemented for pumping fluid through a channel of the microfluidic device, the material from which the microfluidic device is constructed, or the nature of the particles (i.e., organic or inorganic) to be sampled.

It is a still object and feature of the present invention to provide a method of obtaining a sample concentration of particles from a solution in a microfluidic device that does not damage the particles or molecules in the solution to be sampled.

In accordance with the present invention, a method is provided of obtaining a sample concentration of particles from a solution in a microfluidic device. The microfluidic device includes a channel having a reservoir port and a collection port. The reservoir port can be any type of liquid/gas interface. The method includes the step of filling the channel with the solution, the solution having particles therein. A reservoir drop is deposited on the reservoir port of sufficient volume to supply the channel with fluid. The solution at the collection port of the channel is allowed to evaporate such that the particles concentrate at the collection port.

The reservoir drop may be formed from the solution or from another fluid. A portion of the solution adjacent the collection port is removed to obtain the sample concentration. A boundary condition may be introduced adjacent to the collection port to control the evaporation of the solution. The boundary condition may include passing a stream of air over the collection port to facilitate evaporation of the solution or positioning a sorption agent adjacent the collection port to facilitate evaporation of the solution. A second reservoir drop may be deposited at the reservoir port of the channel as the first reservoir drop flows into the channel.

In accordance with a further aspect of the present invention, a method is provided of obtaining a sample concentration. The method includes the step of providing a microfluidic device having a channel therethrough. The channel includes a reservoir port and a collection port. The channel is filled with a fluid having particles therein. A portion of the fluid at the collection port is evaporated so as to generate a pressure gradient between the fluid at the reservoir port and the fluid at the collection port such that the fluid flows through the channel towards the collection port and such that the particles in fluid concentrate at the collection port.

A reservoir drop of a reservoir solution is deposited over the reservoir part of the channel of sufficient dimension to overlap the reservoir port of the channel. It is contemplated that the reservoir solution be the fluid. A second reservoir drop may be deposited at the reservoir port of the channel as the first reservoir drop flows into the channel.

A second portion of the fluid adjacent the collection port may be drawn to obtain the sample concentration. A stream of air may be passed over the collection port to facilitate evaporation of the fluid. Alternatively, a sorption agent may be positioned adjacent the collection port to facilitate evaporation of the fluid.

In accordance with a further aspect of the present invention, a method is provided of obtaining a sample concentration of particles from a solution in a microfluidic device. The microfluidic device includes a channel having a reservoir port of a predetermined radius and a collection port of a predetermined radius. The method includes the step of filling the channel with the solution having particles therein. A reservoir drop is deposited over the reservoir part of the channel such that the solution of the channel flows towards the collection port in response to evaporation of the solution at the collection port. Thereafter, the particles at the collection port may be collected.

The reservoir drop may be formed from the solution or an alternate fluid. The step of collecting the particles includes the additional step of removing a portion of the solution adjacent the collection port to obtain the sample concentration. In order to facilitate evaporation of the solution, a stream of air may be passed over the collection port. Alternatively, a sorption agent may be positioned adjacent to the collection port to facilitate evaporation of the solution. A second reservoir drop may be deposited at the reservoir port of the channel as the first reservoir drop flows into the channel.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
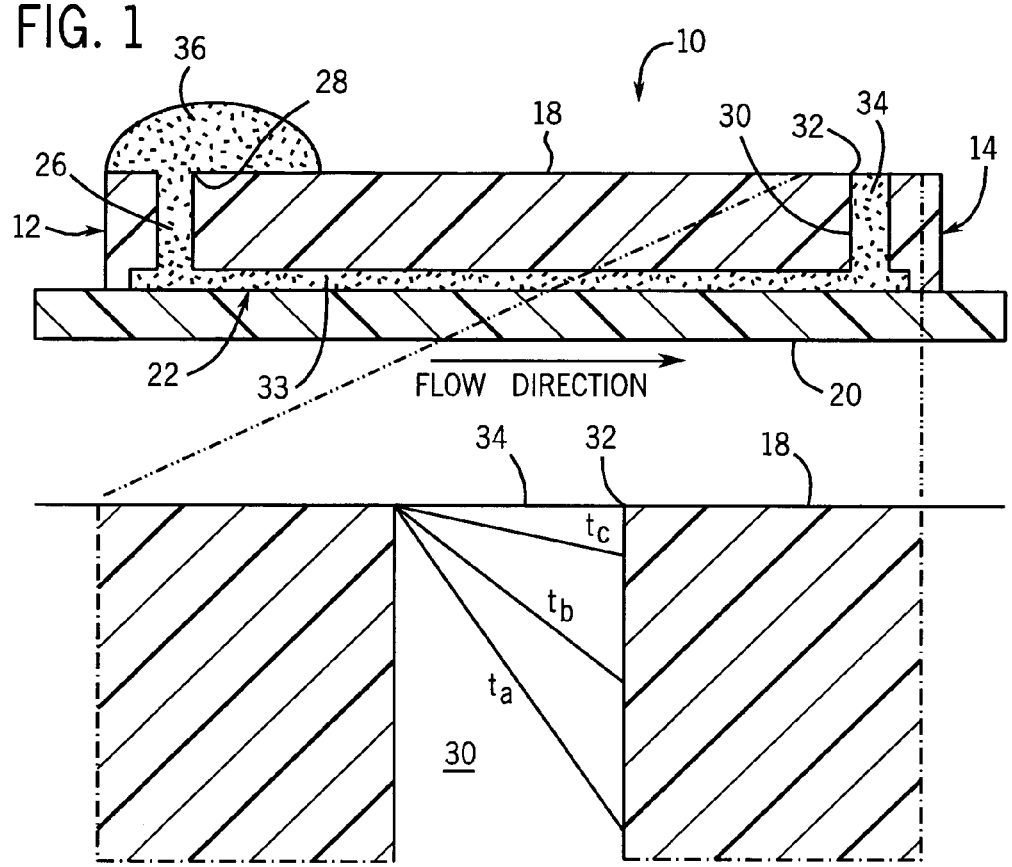
FIG. 1 is an enlarged, schematic view showing the flow of liquid through a microchannel of a microfluidic device.
Figure 2:
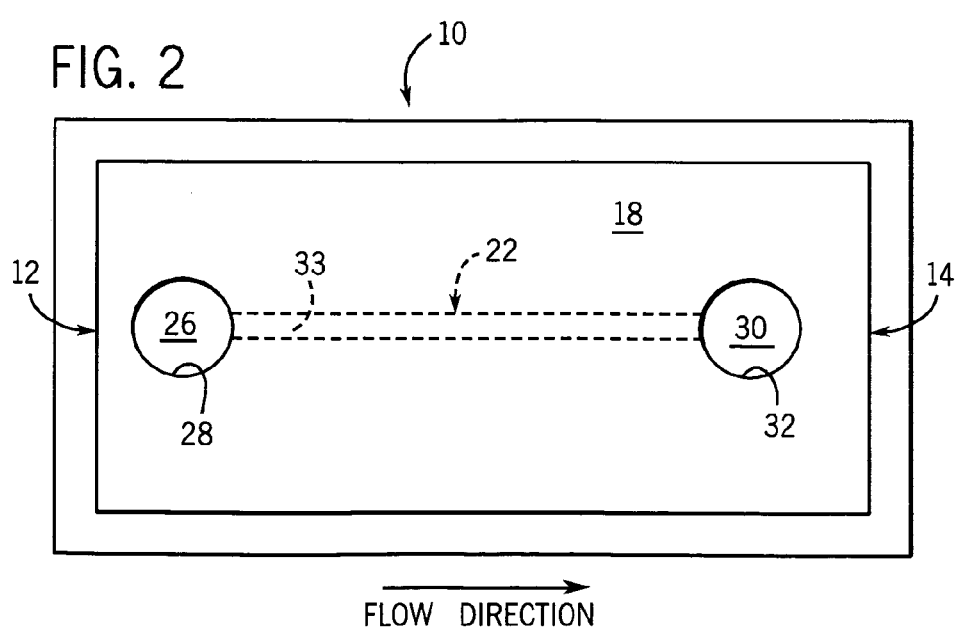
FIG. 2 is a top plan view of the microfluidic device of FIG. 1.

Referring to FIGS. 1–2, a microfluidic device for use in the method of the present invention is generally designated by the reference numeral 10. Microfluidic device 10 is fabricated in a conventional manner from any suitable material such as polydimethylsiloxane (PDMS). It can be appreciated that microfluidic device 10 may be fabricated from other materials without deviating from the scope of the present invention. Microfluidic device 10 has first and second ends 12 and 14, respectively, and upper and lower surfaces 18 and 20, respectively. Microchannel 22 extends through microfluidic device 10 and includes a first vertical portion 26 terminating at reservoir port 28 that communicates with upper surface 18 of microfluidic device 10 and a second vertical portion 30 terminating at collection port 32 that also communicates with upper surface 18 of microfluidic device 10. First and second vertical portions 26 and 30, respectively, of microchannel 22 are interconnected by and communicate with horizontal portion 33 of microchannel 22. The dimensions of microchannel 22 connecting reservoir port 28 and collection port 32 are arbitrary. Further, the reservoir port 28 can be any type of liquid/gas interface having a volume sufficient to supply the microchannel 22 with fluid.

In operation, microchannel 22 is pre-filled with a solution having a concentration of particles therein. A reservoir drop 36 of fluid is placed over reservoir port 28 to continually supply fluid to microchannel 22. Reservoir drop 36 may be formed from the solution provided in microchannel 22 or from a particle-free fluid. Reservoir drop 36 may be deposited over reservoir port 28 in any conventional manner such as by using a handheld pipettes or a robotic micropipetting station. The amount of pressure present within reservoir drop 36 of fluid at an air-liquid interface is given by the Young-LaPlace equation:

$$\Delta P = \gamma(1/R1 + 1/R2) \qquad \text{Equation (1)}$$

wherein $\gamma$ is the surface free energy of the liquid; and R1 and R2 are the radii of curvature for two axes normal to each other that describe the curvature of the surface of reservoir drop 36.

For spherical drops, Equation (1) may be rewritten as:

$$\Delta P = 2\gamma/R \qquad \text{Equation (2)}$$

wherein: R is the radius of reservoir drop 36.

The Young-LaPlace pressure at collection port 32 prevents the solution from exiting microchannel 22 through collection port 32. However, as the solution at collection port 32 evaporates, the meniscus at the interface 34 of the ambient air and the solution moves slightly away from equilibrium. For equilibrium to be re-established, additional solution must flow through microchannel 22 from reservoir port 28 to collection port 32. The volume of the reservoir drop 36 must be sufficient to prevent the evaporation of the solution at reservoir port 28 from inducing any flow of the solution towards reservoir port 28. As such, additional reservoir drops 36 may be deposited over reservoir port 28 to maintain a sufficient volume of fluid over reservoir port 28.

It can be assumed that interface 34 between the ambient air and the solution at collection port 32 is flat such that interface 34 can be modeled as a horizontal plate. Using a transport analogy, the equations for mass transfer can be substituted for the equations of heat transfer. The mass transfer equivalent of the equation for heat transfer from a horizontal plate is:

$$\frac{k_x L}{c_f D} = 0.54 \left[ \frac{L^3 \rho_f^2 g \zeta_f \Delta x_A}{\mu_f^2} \left(\frac{v}{D}\right)_f \right]^{0.25} \qquad \text{Equation 3}$$

wherein: $k_x$ is the mass transfer coefficient of water into air; L is the characteristic length of the collection port air/water interface; $c_f$ is the molar concentration of air; D is the diffusion coefficient of water through air, $\rho_f$ is the density of air, g is the gravitational constant; $\zeta_f$ is the concentration coefficient of volumetric expansion for air; $\Delta x_A$ is the difference in mole concentration of water vapor at the air/water interface and further away at room concentration; $\mu_f$ is the viscosity of air; and $v$ is the kinematic viscosity of air.

Once the mass transfer coefficient, $k_x$, has been calculated, the mass flux from the collection port 32 can be predicted with the equation:

$$W_A = k_x A \frac{x_{A0} - x_{A\infty}}{1 - x_{A0}} \qquad \text{Equation 4}$$

wherein: $W_A$ is the mass flux of water into air from the collection port; $x_{A0}$ is the mole fraction of water vapor at the air/liquid interface; $x_{A\infty}$ is the mole fraction of water vapor in the bulk air of the room; and A is the cross-sectional area of the collection port. The induced flow in microchannel 22 will have a volumetric flow rate equal to $W_A$.

The particles suspended in the solution will flow towards collection port 32 if the bulk fluid velocity is large enough to overcome particle diffusion against the direction of fluid flow. When the particles encounter interface 34 of the ambient air and the solution, the particles will be left behind as the evaporation progresses. As particles collect in collection port 32, a concentration gradient will form. It can be appreciated that a sample concentration of particles can be easily removed from the collection port in any conventional manner or moved to another portion of microfluidic device 10 for further use.

Since evaporation of the solution may be a time consuming process, it is contemplated to introduce a known boundary condition adjacent to collection port 32 to increase the rate at which the solution evaporates and to provide for adequate flow rate of the solution through microchannel 22 that is concentrating a wide variety of particles. By way of example, a sorption agent may be positioned adjacent collection port 32. Alternatively, a stream of air may be directed across interface 34 of the solution and the ambient air at collection port 32.

Even though high concentrations of particles will accumulate in collection port 32, the diffusion of particles down the concentration gradient will be limited because of the velocity of the evaporation-induced fluid flow. To quantify the relative effects of diffusion and convection, the Peclet number is often used. The Peclet number (Pe) is calculated using the equation:

$$Pe = \frac{vl}{D} \quad \text{Equation 5}$$

wherein: D is the diffusion coefficient of the particle; v is the fluid velocity; and l is the characteristic length. For most macromolecules, the diffusion coefficient is so small that even minute fluid velocities are enough to make diffusion negligible. For example, if bovine serum albumin (BSA) is placed in a fluid stream with a velocity of 10 μm/s, diffusion only becomes important when lengths approach 65 μm ($D=6.5\times10^{-7}$ $cm^2/s$, Pe=10).

The flow rate of the solution through microchannel 22 depends on a variety of variables including humidity, temperature and the like. Further, depending on the size of the particles in the solution, it is possible that a low concentration region may develop in the stream flowing through the middle of horizontal portion 33 of microchannel 22 because of the parabolic velocity profile. The velocity profile hinders particle concentration in the sense that larger particles near the walls of microchannel 22 move very slowly towards collection port 32 since their size prevents the particles from readily diffusing towards the center of the stream. As such, it may be necessary to pass several microchannel volumes of particle-free fluid through microchannel 22 in order to completely flush out the particles. Alternatively, if the particles in the solution are smaller, the low concentration region in microchannel 22 does not develop since the particles are small enough to diffuse into the middle of microchannel 22 so as to eliminate any concentration gradient from developing.

In order to increase the flexibility of microfluidic device 10, an air/fluid interface may be created on virtual walls within microchannel 22. Virtual walls may be provided within microchannel 22 by utilizing surface effects to guide the fluid(s) on flow paths to maintain laminar flow. The guiding structure includes flow guide strips formed on opposite surfaces of microchannel 22. The strips are wettable by a selected fluid to direct the fluid from a source location to a destination location. The regions adjacent to the guiding strips with microchannel 22 are non-wettable. The smooth interface between the air and fluid along the flowing stream allows for gas-fluid reactions, such as obtaining a sample of concentration of particles, to take place across the interface.

It can be appreciated that evaporation is a reliable and robust way to concentrate sample particles within microchannel 22 of microfluidic device 10. Various modes of carrying out the invention are contemplated as being within the scope of the following claims particularly pointing out and distinctly claiming the subject matter, which is regarded as the invention.

We claim:

1. A method of obtaining a concentrated sample of a solution in a microfluidic device, the microfluidic device including a channel having a reservoir port and a collection port, comprising the steps of:

filling the channel with the solution, the solution having particles therein;

depositing a reservoir drop on the reservoir port of the channel of sufficient dimension to overlap the reservoir port of the channel and to exert an output pressure on the solution at the reservoir port of the channel; and allowing the solution at the collection port of the channel to evaporate such that the particles concentrate at the collection port.

2. The method of claim 1 comprising wherein the reservoir drop is formed from the solution.

3. The method of claim 1 comprising the additional step of removing a portion of the solution adjacent the collection port to obtain the concentrated sample.

4. The method of claim 1 further comprising the additional step of introducing a boundary condition adjacent the collection port to control the evaporation of the solution.

5. The method of claim 1 further comprising the additional step of passing a stream of air over the collection port to facilitate evaporation of the solution.

6. The method of claim 1 further comprising the additional step of positioning a sorption agent adjacent the collection port to facilitate evaporation of the solution.

7. The method of claim 1 comprising the additional step of sequentially depositing a second reservoir drop at the reservoir port of the channel after the first reservoir drop flows into the channel.

8. A method of obtaining a concentrated sample, comprising the steps of:

providing a microfluidic device having a channel therethough, the channel having a reservoir port and a collection port;

providing fluid in the channel, the fluid having particles therein; and evaporating a portion of the fluid at the collection port so as to generate a pressure gradient between the fluid at the reservoir port and the fluid at the collection port such that the fluid flows through the channel towards the collection port and such that the particles in the fluid concentrate at the collection port.

9. The method of claim 8 comprising the additional step of depositing a reservoir drop of a reservoir solution over the reservoir port of the channel of sufficient dimension to overlap the reservoir port of the channel.

10. The method of claim 9 comprising wherein the reservoir solution is the fluid.

11. The method of claim 9 comprising the additional step of sequentially depositing a second reservoir drop at the reservoir port of the channel as the first reservoir drop flows into the channel.

12. The method of claim 8 comprising the additional step of drawing a second portion of the fluid adjacent the collection port to obtain the concentrated sample.

13. The method of claim 8 further comprising the additional step of passing a stream of air over the collection port to facilitate evaporation of the fluid.

14. The method of claim 8 further comprising the additional step of positioning a sorption agent adjacent the collection port to facilitate evaporation of the fluid.

15. The method of claim 8 wherein the microfluidic device has an outer surface and wherein the reservoir port communicates with the outer surface of the microfluidic device.

16. The method of claim 8 wherein the microfluidic device has an outer surface and wherein the collection port communicates with the outer surface of the microfluidic device.

17. A method of obtaining a concentrated sample of a solution in a microfluidic device, the microfluidic device including a channel having a reservoir port of a predetermined radius and a collection port of a predetermined radius, comprising the steps of:

filling the channel with a solution, the solution having particles therein;

depositing a reservoir drop over the reservoir port of the channel such that the solution in the channel flows toward the collection port in response to evaporation of the solution at the collection port; and collecting the particles at the collection port.

18. The method of claim 17 wherein the reservoir drop is formed from the solution.

19. The method of claim 17 wherein the step of collecting the particles includes the additional step of removing a portion of the solution adjacent the collection port to obtain the concentrated sample.

20. The method of claim 17 further comprising the additional step of passing a stream of air over the collection port to facilitate evaporation of the solution.

21. The method of claim 17 further comprising the additional step of positioning a sorption agent adjacent the collection port to facilitate evaporation of the solution.

22. The method of claim 17 comprising the additional step of depositing a second reservoir drop at the reservoir port of the channel as the first reservoir drop flows into the channel.

* * * * *